United States Patent
Sugita et al.

(10) Patent No.: US 8,178,725 B2
(45) Date of Patent: May 15, 2012

(54) METHOD OF SEPARATING AND COLLECTING OPTICALLY ACTIVE AMINO ACID AMIDE

(75) Inventors: Masaki Sugita, Niigata (JP); Satoshi Nanba, Niigata (JP); Akinori Tanaka, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 548 days.

(21) Appl. No.: 11/912,107

(22) PCT Filed: Apr. 21, 2006

(86) PCT No.: PCT/JP2006/308405
§ 371 (c)(1),
(2), (4) Date: Sep. 3, 2009

(87) PCT Pub. No.: WO2006/115194
PCT Pub. Date: Nov. 2, 2006

(65) Prior Publication Data
US 2009/0318730 A1    Dec. 24, 2009

(30) Foreign Application Priority Data

Apr. 21, 2005  (JP) .................................. 2005-123885
Apr. 22, 2005  (JP) .................................. 2005-125495

(51) Int. Cl.
*C07C 237/06*    (2006.01)
(52) U.S. Cl. ...................................................... 564/198
(58) Field of Classification Search ........................ None
See application file for complete search history.

(56) References Cited

U.S. PATENT DOCUMENTS 4,605,477 A * 8/1986 Doya et al. ..................... 204/530
6,949,658 B2 * 9/2005 Katoh et al. ............... 548/339.1

FOREIGN PATENT DOCUMENTS

EP    0930294 A1    7/1999
JP    2001011034 A    1/2001

OTHER PUBLICATIONS

Communication dated Jan. 31, 2011 in EP Appln. 06745536.0-2103.

* cited by examiner

*Primary Examiner* — Paul A Zucker
(74) *Attorney, Agent, or Firm* — Fitch, Evan, Tabin & Flannery LLP

(57) ABSTRACT

A method for efficiently separating and collecting an optically active amino acid amide and an optically active amino acid from an aqueous solution containing the optically active amino acid amide and the optically active amino acid includes separating and collecting an optically active amino acid amide from an aqueous solution containing the optically active amino acid amide and an optically active amino acid, utilizing a difference in solubility in an organic solvent between the optically active amino acid amide and the optically active amino acid, without desalting the aqueous solution or after desalting the same, under such a condition that a ratio (C/A) of the total equivalent (C) of cations to the total equivalent (A) of anions contained in the aqueous solution falls within the range from 0.95 to 1.05 when the aqueous solution is not desalted, and the range from 0.5 to 1.5 when the aqueous solution is desalted.

9 Claims, No Drawings

METHOD OF SEPARATING AND COLLECTING OPTICALLY ACTIVE AMINO ACID AMIDE

CROSS-REFERENCE TO RELATED APPLICATION

This application is a U.S. national phase application filed under 35 U.S.C. §371 of International Application PCT/JP2006/308405, filed on Apr. 21, 2006, and claims the benefit, and the foreign priority of Japanese Applications JP2005-123885 filed Apr. 21, 2005 and JP2005-125495, filed Apr. 22, 2005 designating the United States, the complete disclosures of all the aforesaid applications are hereby incorporated by reference herein.

TECHNICAL FIELD

The present invention relates to a method for efficiently separating and collecting an optically active amino acid amide from an aqueous solution containing the optically active amino acid amide and an optically active amino acid. More specifically, the present invention relates to a method in which an aqueous solution containing a racemic amino acid amide as a raw material is, for example, subjected to the action of an enzyme that stereoselectively hydrolyzes the amide bond of either one of the optically active substances thereof, optionally followed by desalting the aqueous solution; and then the obtained aqueous solution containing an optically active amino acid amide and an optically active amino acid is subjected to a process that utilizes a difference in solubility between the optically active amino acid amide and the optically active amino acid in an organic solvent so as to simply and effectively separate and collect the optically active amino acid amide with high chemical and optical purity. The optically active amino acid amide is a very important substance as a production intermediate for various industrial chemicals, agricultural chemicals, and pharmaceuticals.

BACKGROUND ART

As a conventional method for separating and collecting an optically active amino acid amide, for example, a method is suggested, which comprises asymmetrically and enzymatically hydrolyzing a racemic amino acid amide to prepare an aqueous solution containing an optically active amino acid amide and an optically active amino acid; adding an organic solvent that is a readily-soluble solvent for the optically active amino acid amide but is a poor solvent for the optically active amino acid to the obtained enzymatically reacted solution or a concentrated product thereof to precipitate the optically active amino acid; and separating the optically active amino acid amide contained in the organic solvent phase (see Patent Document 1, for example).

However, when the above method is applied to an aqueous solution containing not only the optically active amino acid amide and the optically active amino acid but also an acid, base or salt which is originated from the raw material for the amino acid amide or an aqueous solution of microorganism cells or enzymes used as catalysts, a problem occurs such that yield or chemical purity of the optically active amino acid amide is deteriorated because even after the addition of the organic solvent which is readily-soluble for the optically active amino acid amide and poor for the optically active amino acid to the obtained enzymatically reacted solution or a concentrated product thereof, the optically active amino acid amide to be soluble and the optically active amino acid to be insoluble are not properly charged electrically, thereby decreasing the content of the optically active amino acid amide in the organic solvent phase and allowing contamination with the optically active amino acid.

Patent Document 1: Japanese Patent Laid-Open No. 2001-11034

DISCLOSURE OF THE INVENTION

Problem to be Solved by the Invention

An object of the present invention is to solve the above problem of prior art and to establish and provide a method which can effectively and simply separate and collect an optically active amino acid amide with high purity from an aqueous solution obtained by, for example, processing an aqueous solution of a racemic amino acid amide with biocatalysts such as cells of microorganism or enzymes that stereoselectively hydrolyze the amide bond of either D- or L-form of optically active amino acid amide.

Means for Solving the Problems

In order to solve the above problem, the present inventors have attempted to obtain an optically active amino acid amide by adjusting a pH of the aqueous solution to an isoelectric point pH expected from an acid-base dissociation equilibrium constant of the optically active amino acid amide so that the largest amount of free optically active amino acid amide would move to an organic solvent phase; and then adding an organic solvent that is readily-soluble for the optically active amino acid amide but poor for the optically active amino acid to a concentrated product of the adjusted solution. However, only the adjustment to the isoelectric point pH results in insufficient movement of the optically active amino acid amide to the organic solvent phase, thereby largely decreasing yield of the obtained optically active amino acid amide because volatile ion substances such as ammonia and alkylamines which are generated by asymmetrical hydrolysis of the amino acid amide as a raw material are distilled away from the system. Thus, it has been found that the above process cannot solve the problem.

Then, as a result of further intensive researches for solving the above problems, the present inventors have found that a highly-pure optically active amino acid amide contaminated with very little amount of an optically active amino acid or salt can be effectively and simply obtained by analyzing concentrations of ions contained in an aqueous solution processed with a biocatalyst such as cells of microorganism or an enzyme; adding counter ions to supplement deficient ions, if any, so that the ratio (C/A) of the total equivalent (C) of cations to the total equivalent (A) of anions contained in the aqueous solution falls within a specific range; dehydrating the aqueous solution by azeotropic distillation or dehydration-concentration to replace water with an organic solvent that dissolves the optically active amino acid amide and hardly dissolves the optically active amino acid and inorganic salts; and separating the resultant organic solvent phase containing the optically active amino acid amide from a solid phase containing the precipitated optically active amino acid.

Further, it has been found that when acids, bases, or salts are present together with an optically active amino acid amide and an optically active amino acid in an aqueous solution processed with an enzyme or the like, solubility of the optically active amino acid amide in an organic solvent is decreased or solubility of the optically active amino acid in an organic solvent is increased due to influences of acids or bases, and the amount of optically active amino acid amide attached to salts precipitated as solids is increased, thereby deteriorating purity and yield of the obtained optically active amino acid amide.

Then, the present inventors have made intensive researches to establish a production method in which an optically active amino acid amide is excellently separated from an optically active amino acid and the amount of salts contaminating the optically active amino acid obtained as a solid can be decreased. As a result, they have found that an optically active amino acid amide can be obtained with high purity and in high yield by neutralizing an aqueous solution processed with a biocatalyst such as cells of microorganism or an enzyme, if necessary; desalting the aqueous solution by electrodialysis using an ion exchange membrane with addition of ammonia; analyzing concentrations of ions contained in the obtained aqueous solution; adding counter ions to supplement deficient ions, if any, so that the ratio (C/A) of the total equivalent (C) of cations to the total equivalent (A) of anions contained in the aqueous solution falls within a specific range; dehydrating the aqueous solution by azeotropic distillation or dehydration-concentration to replace water with an organic solvent that dissolves the optically active amino acid amide and hardly dissolves the optically active amino acid; and separating an organic solvent phase containing the resultant optically active amino acid amide from a solid phase composed of the precipitated optically active amino acid.

Thus, the present invention provides a method for separating and collecting an optically active amino acid amide from an aqueous solution containing the optically active amino acid amide and an optically active amino acid by a process utilizing a difference in solubility between the optically active amino acid amide and the optically active amino acid in an organic solvent, characterized in that it comprises changing the aqueous solution to an organic solvent solution by azeotropic distillation with an organic solvent or by dehydration-concentration followed by addition of an organic solvent under such a condition that a ratio (C/A) of the total equivalent (C) of cations to the total equivalent (A) of anions contained in the aqueous solution falls within a range indicated by the following numerical formula (1); and performing solid-liquid separation of an organic solvent phase containing the resultant optically active amino acid amide from a precipitated solid phase containing the optically active amino acid.

$$1-0.05X \leqq C/A \leqq 1+0.05X \quad (1)$$

(In the above numerical formula (1), X is 1 when the aqueous solution is not desalted and X is 10 when the aqueous solution is desalted; and A and C exclude the equivalent of the optically active amino acid amide and optically active amino acid, hydrogen ions and hydroxide ions, and anions and cations derived from ion substances that are distilled away during azeotropic distillation or dehydration-concentration.)

In an embodiment of the present invention wherein the aqueous solution is desalted, the change to the organic solvent solution is preferably conducted under such a condition that the ratio (C/A) of the total equivalent (C) of cations to the total equivalent (A) of anions contained in the aqueous solution falls within a range indicated by the following numerical formula (1').

$$1-0.05X \leqq C/A \leqq 1+0.05X \quad (1')$$

(In the above numerical formula (1'), X represents B/A and is 10 or less where B/A>1; and B is an equivalent of the optically active amino acid amide contained in the aqueous solution.)

In an embodiment of the present invention wherein the aqueous solution is desalted, the aqueous solution is preferably prepared by desalting an aqueous solution containing an optically active amino acid amide and an optically active amino acid by electrodialysis using an ion exchange membrane. Further, the aqueous solution is more preferably prepared by adding ammonia to an aqueous solution containing an optically active amino acid amide and an optically active amino acid; and desalting the mixture by electrodialysis using an ion exchange membrane. Here, ammonia is preferably added in an amount of 0.01 to 100 times by mole the optically active amino acid amide contained in the aqueous solution.

The present invention is suitable for a case where the optically active amino acid amide is L-amino acid amide represented by the following general formula (1).

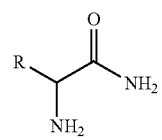

(1)

(In the general formula (1), R represents a $C_{1-4}$ lower alkyl group, a phenyl group, or a benzyl group.)

Further, the present invention is suitable for a case where the optically active amino acid is D-amino acid represented by the following general formula (2).

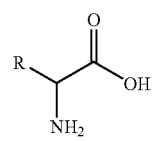

(2)

(In the general formula (2), R represents a $C_{1-4}$ lower alkyl group, a phenyl group, or a benzyl group.)

L-amino acid amide represented by the above general formula (1) typically includes L-2-amino-n-butyric acid amide. D-amino acid represented by the above general formula (2) typically includes D-2-amino-n-butyric acid.

According to a preferred embodiment of the present invention, the organic solvent is at least one member selected from the group consisting of isobutyl alcohol, n-heptyl alcohol, and 2-ethyl-1-hexanol.

Further, according to another preferred embodiment of the present invention, the ion substance distilled away by azeotropic distillation or dehydration-concentration is ammonia or alkylamines.

Effects of the Invention

A highly-pure optically active amino acid amide can be obtained in high yield by analyzing concentrations of anions and cations in an aqueous solution containing an optically active amino acid amide and an optically active amino acid as it is or after neutralization and desalting if necessary; distilling water under such a condition that the concentration ratio of cations to anions contained in the aqueous solution fall within a specific range to replace water with an organic solvent that is readily-soluble for the optically active amino acid amide and poor for the optically active amino acid; performing solid-liquid separation of an organic solvent containing the optically active amino acid amide from slurry precipitates containing the optically active amino acid by means of filtration or the like; and further concentrating the obtained organic solvent phase and drying the obtained solid phase.

In an embodiment of the present invention wherein an aqueous solution containing an optically active amino acid amide and an optically active amino acid is used as it is without desalting, the aqueous solution which has been processed using a biocatalyst such as an enzyme and has contained contaminants such as acids, bases and salts does not have to be subjected to removal of impurities to separate and collect a highly-pure optically active amino acid amide, thus providing an industrial advantage for process simplification.

BEST MODE FOR CARRYING OUT THE INVENTION

Hereafter, embodiments of the present invention will be described in detail. Types of optically active amino acid amides and optically active amino acids to be used in the present invention are not particularly limited. Both natural and non-natural types of optically active amino acid amides and optically active amino acids may be used. Examples thereof include 2-amino-n-butyric acid amide and 2-amino-n-butyric acid, t-leucine amide and t-leucine, and valine amide and valine. However, optically active amino acid amides and optically active amino acids other than the above examples, or an optically active amino acid amide and an optically active amino acid which are different in amino acid structure from each other may be used.

An aqueous solution containing an optically active amino acid amide and an optically active amino acid can be obtained, for example, by subjecting an aqueous solution of a racemic amino acid amide to the action of a biocatalyst such as cells of microorganism that stereoselectively hydrolyzes the amide bond of either D- or L-amino acid amide or an enzyme obtained from a processed product of the cells. The microorganism is not particularly limited, and examples thereof include those belonging to the genus *Rhodococcus*, the genus *Pseudomonas*, the genus *Ochrobactrum*, and the genus *Serratia*. Specific examples include *Rhodococcus erythropolis* NR28 (FERM P-8938), *Pseudomonas fluorescens* IFO12055, *Ochrobactrum anthropi* ATCC49237, and *Serratia marcescens* IAM12143. In addition, both mutant strains derived from these microorganisms by artificial mutagenesis, and recombinant strains derived by genetic procedures such as cell fusion and gene recombination, may be used, as long as they are capable of asymmetrically hydrolyzing the amide bond of amino acid amides. These microorganisms are used in a form of cells or processed products of cells including dried cells, crushed cells, cell extracts, crude or purified enzymes, and those immobilized to carriers.

The above optical resolution method using the reaction of a biocatalyst such as an enzyme may be conducted by, for example, bringing the above cell or processed product of cells into contact with an aqueous solution in which a racemic amino acid amide is dissolved as a material substrate. Usually, the amino acid amide as a substrate has a concentration of 0.01 wt % to a saturated concentration, preferably 1 to 25 wt % from the viewpoint of operability or production efficiency. The concentration of the cell or processed product thereof used as a catalyst may be varied depending on specific activity or activity thereof. Usually, the amount thereof is preferably 1/1000 to 1/10 times, and more preferably 1/500 to 1/20 times the weight of the amino acid amide as a raw material. The pH of the reaction solution is preferably 4 to 11, more preferably 6 to 10. The reaction temperature is preferably 10 to 60° C., more preferably 30 to 40° C. The reaction may be performed until either D- or L-amino acid amide contained in the racemic amino acid amide is converted to a corresponding optically active amino acid. After the reaction, the cells or processed product thereof are removed from the reaction solution by known methods such as centrifugation and filtration to obtain an aqueous solution containing an optically active amino acid amide and an optically active amino acid.

In the case of desalting the aqueous solution, the desalting method is not particularly limited, but the desalting can be efficiently performed, for example, by electrodialysis using an ion exchange membrane. In the case of performing the desalting by electrodialysis, the aqueous solution containing an optically active amino acid amide and an optically active amino acid is neutralized before desalting, if necessary. Thereafter, ammonia is added to the solution in an amount of 0.01 to 100 times by mole, preferably 3 to 10 times by mole the optically active amino acid amide before electrodialysis is performed, thereby preventing a loss of the optically active amino acid amide.

The desalting ratio after desalting can be approximately obtained by the numerical formula (2) using an electric conductivity (C1) of the desalted aqueous solution, an initial electric conductivity (C2) before desalting, and an electric conductivity (C3) at the time when desalting is completed to come to equilibrium.

$$Y=\{(C2-C1)/(C2-C3)\}\times 100 \qquad (2)$$

(wherein the desalting ratio (Y) is defined as a ratio of a total mole number of ion species forming salts removed by desalting to a total mole number of ion species forming salts present in the aqueous solution before desalting.)

It is not necessary to continue the desalting until ion species forming the salts are completely removed, but the desalting is preferably performed in a desalting ratio of 50 to 90%. When the desalting ratio is less than 50%, the amounts of acids and bases to be used for ion ratio adjustment and the resulting salts are increased. On the other hand, when the desalting ratio increases up to greater than 90%, the amounts of acids and bases to be used for ion ratio adjustment are decreased but a longer time period for desalting is required, thereby reducing efficiency of use of dialysis membranes and increasing operation cost. It also causes decrease in yield of the optically active amino acid amide after desalting dialysis.

Namely, when the enzymatically processed aqueous solution containing an acid, a base, and a salt in addition to an optically active amino acid amide and an optically active amino acid is used, the use of desalting by electrodialysis using an ion exchange membrane in combination with the adjustment of concentration ratio of ions in the aqueous solution allows the desalting to be terminated at a relatively early stage whereby the desalting by electrodialysis proceeds very rapidly and does not decrease the yield of the optically active amino acid amide. Meanwhile, the use of the desalting process in combination can provide a synergetic effect such that the adjustment of concentration ratio of ions can be made in a relatively wide selection range of the ratio.

The concentrations of anion and cation in the thus-obtained desalted or non-desalted aqueous solution containing the optically active amino acid amide and the optically active amino acid are measured by an ion concentration analysis method such as an ion chromatography and an ICP emission spectrometry. Next, the ratio (C/A) of the total equivalent (C) of cations to the total equivalent (A) of anions contained therein is adjusted to meet the range of the numerical formula (1) by optional addition of a counter ion substance.

When the aqueous solution is not desalted, X is 1 in the numerical formula (1), and thus the ratio (C/A) is adjusted to meet the range of 0.95≦C/A≦1.05, more preferably 0.975≦C/A≦1.025. When C/A is lower than 0.95, a greater proportion of optically active amino acid amides form salts with anions, thereby decreasing the solubility of optically active amino acid amides in an organic solvent and remarkably reducing the yield of optically active amino acid amides. On the other hand, when C/A exceeds 1.05, the solubility of optically active amino acid amides in an organic solvent does not decrease but a greater proportion of optically active amino acids form salts with cations, thereby increasing the solubility of optical amino acids in an organic solvent and producing only a lower purity of optically active amino acid amides containing a large amount of optically active amino acids.

Further, when the aqueous solution is desalted, X is 10 in the numerical formula (1), and thus the ratio (C/A) is adjusted to meet the range of 0.5≦C/A≦1.5. Preferably, the ratio (C/A) is adjusted to meet the range of the following numerical formula (1') depending on the degree of desalting.

$$1-0.05X \leq C/A \leq 1+0.05X \quad (1')$$

(In the above numerical formula (1'), X represents B/A and is 10 or less wherein B/A>1; and B is an equivalent of optically active amino acid amides contained in the aqueous solution.)

When the desalting ratio is 50% (or B/A=2), the above ratio (C/A) is preferably adjusted to fall within 0.9≦C/A≦1.1. When the desalting ratio is 90% (or B/A=10), the ratio is preferably adjusted to fall within 0.5≦C/A≦1.5.

As described above, it is preferable that C/A does not become lower than 0.9 when the desalting ratio is 50%, and C/A does not become lower than 0.5 when the desalting ratio is 90%. This prevents the solubility of optically active amino acid amides in an organic solvent from decreasing. Further, it is preferable that C/A does not exceed 1.1 when the desalting ratio is 50%, and C/A does not exceed 1.5 when the desalting ratio is 90%. In these cases, there are no influences on the solubility of optically active amino acid amides in an organic solvent, and cation salts formed by optically active amino acids decrease so that optically active amino acids are prevented from contaminating the organic solvent. When the desalting ratio is a percentage other than the above, the upper and lower limits in the above formula (1') have the same significances as above.

Ion substances that are included in the total equivalents of ions are nonvolatile ion substances remaining in the system after the aqueous solution is changed to the organic solvent solution, and thus exclude volatile ion substances, for example, those liberated and distilled during concentration operation. For example, ammonia and alkylamines, which are weaker basic than the optically active amino acid amide contained in the aqueous solution or the bases used for adjustment of concentration ratio of ions are not counted as the anion since they are distilled away from the system.

Further, hydrogen ions and hydroxide ions, which are derived from water present in the reaction solution, are excluded from ion species. Furthermore, optically active amino acid amides and optically active amino acids per se are intended to be kept in neutrally-charged free state, and thus are not counted as ion substances.

Examples of the counter ion substance to be used for adjusting the ion concentration ratio C/A include mineral acids such as HCl, $HNO_3$, and $H_2SO_4$, and other acids such $H_3PO_4$ when anions are deficient; and hydroxides of alkali metals such as KOH and NaOH when cations are deficient. The ion concentration ratio C/A may be adjusted by addition thereof. The adjustment of the ion concentration ratio may be performed either at a stage before or during the replacement with the organic solvent which is readily-soluble for the optically active amino acid amide and poor for the optically active amino acid.

Next, the replacement of the solvent with an organic solvent that dissolves the optically active amino acid amide and hardly dissolves the optically active amino acid, namely the solvent which is readily-soluble for the optically active amino acid amide and poor for the optically active amino acid, is performed. Examples of the organic solvent which is readily-soluble for the optically active amino acid amide and poor for the optically active amino acid include methanol, ethanol, n-propanol, n-butanol, n-pentanol, n-hexanol, n-heptanol, isopropyl alcohol, isobutyl alcohol, and 2-ethyl-1-hexanol.

The change from the aqueous solution to the organic solvent solution can be performed by, for example, a method in which water is removed by concentrating or drying the aqueous solution under ordinary pressure or under a reduced pressure that is set taking into account of temperature stability of the optically active amino acid amide; and an organic solvent that is readily-soluble for the optically active amino acid amide and poor for the optically active amino acid is added.

Further, the organic solvent which is readily-soluble for the optically active amino acid amide and poor for the optically active amino acid is preferably one that has an azeotropic property with water. Among the above-listed solvents, examples of such an organic solvent include ethanol, n-propanol, n-butanol, n-pentanol, n-hexanol, n-heptanol, isobutyl alcohol, and 2-ethyl-1-hexanol. In particularly, as more preferred organic solvents, mention may be made of isobutyl alcohol, n-heptyl alcohol, and 2-ethyl-1-hexanol. The above organic solvents from ethanol to 2-ethyl-1-hexanol have azeotropic temperatures with water of 78° C., 88° C., 93° C., 96° C., 98° C., 99° C., 90° C., and 99° C., respectively, under ordinary pressure.

Exemplary methods for supplying an organic solvent for azeotropic distillation include a method in which a required amount of solvent is fed in advance, and a method in which a solvent is added while distillation is performed. The latter method may be conducted in a manner of one-pass distillation in which a fresh solvent is always supplied, or a manner in which water is removed using a decanter from a recovered solution which is trapped by distillation and composed of water and the organic solvent, and the upper organic solvent layer is refluxed for reuse. These solvent replacement operations allow the optically active amino acid amide soluble in the solvent to be dissolved in an organic solvent phase while the optically active amino acid or salts insoluble in the solvent are precipitated as a slurry solid phase.

The change from the aqueous solution to the organic solvent solution is desirably continued until the water content becomes preferably 0.5 wt % or less, more preferably 0.1 wt % or less relative to the total amount of the organic solvent phase and the solid phase. When the water content exceeds 0.5%, insoluble optically active amino acids or salts are not sufficiently precipitated, and as a result, the purity of optically active amino acid amides contained in the organic solvent phase is lowered.

After the aqueous solution is changed to the organic solvent solution in the above way, the organic solvent phase containing the optically active amino acid amide and the slurry solid phase composed of the optically active amino acid or salts are subjected to solid-liquid separation by means of centrifugation, filtration, or the like. Further, the solids are washed with the organic solvent, and the resulting organic solvent solutions are concentrated and cooled to produce highly-pure optically active amino acid amides in high yield.

EXAMPLES

Hereafter, the present invention will be specifically explained by way of Examples and Comparative Examples, but not limited to these Examples.

Examples I-1 to I-3 and Comparative Examples I-1 to I-3

1. Preparation of Cell Suspension for Enzymatic Reaction

According to Japanese Patent Laid-open No. 2002-253294 which discloses a method for producing an optically active aliphatic amino acid amide, a cell suspension for enzymatic reaction was prepared using *Ochrobactrum anthropi* ATCC49237 strain cells that were cultured and isolated.

2. Preparation of Enzymatically Processed Aqueous Solution of Amino Acid Amide 353 g (2.55 mol) of D,L-2-amino-n-butyric acid amide hydrochloride was dissolved in 1000 g of water, and the pH of the solution was adjusted with a 48 wt % NaOH aqueous solution to 7 which was an optimum pH for enzymatic reaction. Further, water was added to the solution till it weighed 2000 g in total. A cell suspension equivalent to 2.6 g of cells on dry weight basis was added to 2000 g of the aqueous solution of D,L-2-amino-n-butyric acid amide hydrochloride to allow the reaction to proceed at 40° C. for 22 hours. After the reaction, the reacted solution was subjected to centrifugation to remove insoluble matters derived from cells, thereby providing an enzymatically processed aqueous solution of amino acid amide.

As a result of analysis by HPLC of the enzymatically reacted solution, it was found that only D-2-amino-n-butyric butyric acid amide in the raw material was quantitatively converted to D-2-amino-n-butyric acid at a yield of 100%. Deamidated D-2-amino-n-butyric acid and unreacted L-2-amino-n-butyric acid amide both had a concentration of 6.3 wt % in the aqueous solution, and thus the reaction proceeded stereoselectively.

3. Analysis of Species and Concentration of Ions in Enzymatically Reacted Solution The aqueous solution containing L-2-amino-n-butyric acid amide and D-2-amino-n-butyric acid obtained by the enzymatic reaction was analyzed by an ion chromatography in terms of species and concentration of ions coexisting in the solution. $Cl^-$ and $Na^+$ accounted for almost all the anion and cation therein, respectively. $Cl^-$ ion had a concentration of 7.03 wt % (0.198 mol per 100 g of solution), and $Na^+$ ion had a concentration of 0.61 wt % (0.027 mol per 100 g of solution). According to the results, the concentration ratio of $Na^+$ ion to $Cl^-$ ion was 0.136. It was confirmed that the concentration ratio of these ions contained in the enzymatically reacted aqueous solution was unbalanced so that anions are excessive.

4. Relation Between Ion Concentration Ratio and Isolation Of Optically Active Amino Acid Amide 100 mL of the enzymatically reacted solution was dispensed for each of Examples I-1 to I-3 and Comparative Examples I-1 to I-3. One of them had a concentration ratio $Na^+/Cl^-$ of 0.14 without adjustment, while the concentration ratios of the others were adjusted to 0.95, 1.00, 1.05, 1.10, and 1.15 using a 48 wt % NaOH aqueous solution. Then, the obtained solutions were concentrated by rotary evaporators. After the concentration, 100 mL of isobutyl alcohol, which is a readily-soluble solvent for L-2-amino-n-butyric acid amide and a poor solvent for D-2-amino-n-butyric acid, was mixed with the obtained concentrate. The mixture was concentrated by azeotropic dehydration with a rotary evaporator. After the evaporation to dryness, 100 mL of isobutyl alcohol was added again, providing an organic solvent solution containing slurry white crystals. The organic solvent solution containing slurry white crystals was well stirred, from which a sample was taken. It was confirmed that the sample had a water content of 0.5 wt % or less. Next, the slurry white crystals were isolated by suction filtration, and further 30 mL of isobutyl alcohol was added thereto for washing, followed by collecting the mother liquor thereof. The filtrate was concentrated with the rotary evaporator and dried in a vacuum at 40° C., yielding needle crystals of L-2-amino-n-butyric acid amide. Table 1 shows the relation between the adjusted ion concentration ratio and the yield and purity of the obtained L-2-amino-n-butyric acid amide. The range of ion concentration ratio of 0.95 to 1.05 provided optimum results in both the yield and chemical purity of the optically active amino acid amide.

TABLE 1

Relation between the ion concentration ratio in the enzymatically reacted aqueous solution and the yield and chemical purity of the obtained L-2-amino-n-butyric acid amide

| Samples | Ion molar ratio ($Na^+/Cl^-$) | Yield [%] | Chemical purity [%] |
|---|---|---|---|
| Comparative Example I-1 | 0.14 | less than 0.1 | less than 20 |
| Example I-1 | 0.95 | 80.2 | 98.7 |
| Example I-2 | 1.00 | 88.2 | 99.0 |
| Example I-3 | 1.05 | 96.0 | 80.2 |
| Comparative Example I-2 | 1.10 | 97.7 | 69.8 |
| Comparative Example I-3 | 1.15 | 95.3 | 62.1 |

Comparative Example I-4

500 g of the enzymatically reacted aqueous solution obtained by the method of Example I-1, containing L-2-amino-n-butyric acid amide and D-2-amino-n-butyric acid, was adjusted using a 48 wt % NaOH aqueous solution to the pH of 8.5 at which the amount of free L-2-amino-n-butyric acid amides is maximized. In this instance, the ion concentration ratio $Na^+/Cl^-$ was 0.56. The aqueous solution was processed in the same manner as in the above Examples I-1 to I-3 and Comparative Examples I-1 to I-3 except the ion concentration ratio. The obtained L-2-amino-n-butyric acid amide had a yield of 0.76% and a purity of 60.4%, both of which were insufficient.

Examples II-1 to II-4, Comparative Examples II-1 to II-2

1. Preparation of Cell Suspension for Enzymatic Reaction

The preparations were carried out in the same manner as in the above Examples I-1 to I-3 and Comparative Examples I-1 to I-3.

2. Preparation of Enzymatically Processed Aqueous Solution of Amino Acid Amide The preparations were carried out in the same manner as in the above Examples I-1 to I-3 and Comparative Examples I-1 to I-3.

As a result of analysis by HPLC of the enzymatically reacted solution, it was found that only D-2-amino-n-butyric acid amide in the raw material was quantitatively converted to D-2-amino-n-butyric acid at a yield of 100%. Deamidated D-2-amino-n-butyric acid and unreacted L-2-amino-n-butyric acid amide both had a concentration of 6.3 wt % in the aqueous solution, and thus the reaction proceeded stereoselectively.

3. Desalting of Enzymatically Reacted Solution 245 g of 25% ammonia water was added to 1200 g of the enzymatically reacted aqueous solution containing L-2-amino-n-butyric acid amide and D-2-amino-n-butyric acid, and the mixture was desalted until the concentration of the remaining salts became 10% relative to the salt concentration before electrodialysis. The aqueous solution after desalting weighed 1095 g, and contained L-2-amino-n-butyric acid amide and D-2-amino-n-butyric acid, both of which had a concentration of 7 wt %. Yields of L-2-amino-n-butyric acid amide and D-2-amino-n-butyric acid were both 97%.

4. Analysis of Species and Concentration of Ions in Desalted Aqueous Solution The desalted aqueous solution containing L-2-amino-n-butyric acid amide and D-2-amino-n-butyric acid was analyzed by an ion chromatography in terms of species and concentration of ions present in the solution. $Cl^-$ and $Na^+$ accounted for almost all the anion and cation therein, respectively. $Cl^-$ had a concentration of 0.776 wt % (0.0216 mol per 100 g of aqueous solution), and $Na^+$ had a concentration of 0.178 wt % (0.00774 mol per 100 g of aqueous solution). The ion concentration ratio $Na^+/Cl^-$ was 0.358. It was confirmed that the anion was excessive compared with the cation.

5. Relation Between Ion Concentration Ratio and Isolation Of Optically Active Amino Acid Amide 50 g of the desalted aqueous solution was dispensed for each of Examples II-1 to II-4 and Comparative Examples II-1 and II-2. A 48 wt % NaOH aqueous solution was added to the solutions so that the solutions had ion concentration ratios $Na^+/Cl^-$ of 0.36, 0.50, 0.80, 1.0, 1.5, and 2.0. Then, the obtained solutions were concentrated by rotary evaporators. After the concentration, 50 mL of isobutyl alcohol was mixed therewith, and the mixture was concentrated by azeotropic dehydration with a rotary evaporator. 50 mL of isobutyl alcohol was added thereto again, providing an organic solvent solution containing slurry white crystals. The organic solvent solution containing slurry white crystals was well stirred, from which a sample was taken. It was confirmed that the sample had a water content of 0.5 wt % or less. Next, the slurry white crystals were isolated by suction filtration, and further 20 mL of isobutyl alcohol was added thereto for washing, followed by collecting the mother liquor thereof. The filtrate was concentrated with the rotary evaporator and the obtained concentrate was dried in a vacuum at 40° C., yielding needle crystals of L-2-amino-n-butyric acid amide. Table 2 shows the adjusted ion concentration ratio and the yield and purity obtained at the ratio. When the desalting was performed to achieve a desalting ratio of 90%, optimum results of both yield and chemical purity of the obtained optically active amino acid amide were obtained in the range of ion concentration of 0.5 to 1.5.

TABLE 2

Relation between the yield and chemical purity of L-2-amino-n-butyric acid amide and the ion concentration ratio adjustment combined with desalting dialysis.

| Samples | Ion molar ratio ($Na^+/Cl^-$) | Yield [%] | Chemical purity [%] |
|---|---|---|---|
| Comparative Example II-1 | 0.36 | 86.2 | 97.4 |
| Example II-1 | 0.5 | 95.6 | 97.2 |
| Example II-2 | 0.8 | 99.8 | 97.6 |
| Example II-3 | 1.0 | 99.2 | 99.1 |
| Example II-4 | 1.5 | 99.3 | 98.5 |
| Comparative Example II-2 | 2.0 | 99.3 | 40.1 |

INDUSTRIAL APPLICABILITY

The present invention is a method for effectively and simply separating and collecting an optically active amino acid amide with excellent chemical and optical purities. The method is useful for producing an optically active amino acid amide which is a very important substance as an intermediate in the production of various industrial chemicals, agricultural chemicals, and pharmaceuticals.

The invention claimed is:

1. A method for separating and collecting an optically active amino acid amide from an aqueous solution containing the optically active amino acid amide and an optically active amino acid by a process utilizing a difference in solubility between the optically active amino acid amide and the optically active amino acid in an organic solvent, which comprises Changing the aqueous solution to an organic solvent solution by azeotropic distillation with an organic solvent or by dehydration-concentration followed by addition of an organic solvent under such a condition that a ratio (C/A) of the total equivalent (C) of cations to the total equivalent (A) of anions contained in the aqueous solution falls within a range indicated by the following numerical formula (1), $$1-0.05X < C/A < 1+0.05X \quad (1)$$

wherein X is 1 when the aqueous solution is not desalted and X is 10 when the aqueous solution is desalted; and A and C exclude the equivalent of the optically active amino acid amide and optically active amino acid, hydrogen ions and hydroxide ions, and anions and cations that are distilled away during azeotropic distillation or dehydration-concentration, and performing solid-liquid separation of an organic solvent phase containing the resultant optically active amino acid amide from a precipitated solid phase containing the optically active amino acid, wherein the optically active amino acid amide is L-amino acid amide represented by the following chemical formula (1),

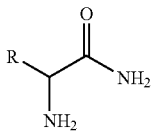
(1)

wherein R represents a $C_{1-4}$ lower alkyl group, a phenyl group, or a benzyl group, and
wherein the optically active amino acid is D-amino acid represented by the following chemical formula (2),

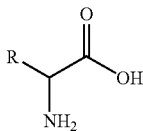
(2)

wherein R represented a $C_{1-4}$ lower alkyl group, a phenyl group, or a benzyl group.

2. The method for separating and collecting an optically active amino acid amide according to claim 1,
wherein when the aqueous solution is desalted, the change to the organic solvent solution is conducted under such a condition that the ratio (C/A) of the total equivalent (C) of cations to the total equivalent (A) of anions contained in the aqueous solution falls within a range indicated by the following numerical formula (1'), $$1-0.05X \leq C/A \leq 1+0.05X \quad (1')$$

wherein X represents B/A and is 10 or less where B/A>1; and B is an equivalent of the optically active amino acid amide contained in the aqueous solution.

3. The method for separating and collecting an optically active amino acid amide according to claim 1, wherein the aqueous solution is prepared by desalting an aqueous solution containing an optically active amino acid amide and an optically active amino acid by electrodialysis using an ion exchange membrane.

4. The method for separating and collecting an optically active amino acid amide according to claim 3, wherein the aqueous solution is prepared by adding ammonia to an aqueous solution containing an optically active amino acid amide and an optically active amino acid; and desalting the mixture by electrodialysis using an ion exchange membrane.

5. The method for separating and collecting an optically active amino acid amide according to claim 4, wherein ammonia is added in an amount of 0.01 to 100 times by mole the optically active amino acid amide contained in the aqueous solution.

6. The method for separating and collecting an optically active amino acid amide according to claim 1, wherein the L-amino acid amide represented by the above general formula (1) is L-2-amino-n-butyric acid amide.

7. The method for separating and collecting an optically active amino acid amide according to claim 1, wherein the D-amino acid represented by the above general formula (2) is D-2-amino-n-butyric acid.

8. The method for separating and collecting an optically active amino acid amide according to claim 1, wherein the organic solvent is at least one member selected from the group consisting of isobutyl alcohol, n-heptyl alcohol, and 2-ethyl-1-hexanol.

9. The method for separating and collecting an optically active amino acid amide according to claim 1, wherein the ion substances distilled away during azeotropic distillation or dehydration-concentration is ammonia or alkylamines.

* * * * *